(12) United States Patent
Bouadi

(10) Patent No.: US 8,529,568 B2
(45) Date of Patent: Sep. 10, 2013

(54) SURGICAL CUTTING TOOL

(75) Inventor: Hacene Bouadi, Palo Alto, CA (US)

(73) Assignee: ConforMIS, Inc., Bedford, MA (US)

( * ) Notice: Subject to any disclaimer, the term of this patent is extended or adjusted under 35 U.S.C. 154(b) by 428 days.

(21) Appl. No.: 12/759,988

(22) Filed: Apr. 14, 2010

(65) Prior Publication Data

US 2010/0234849 A1    Sep. 16, 2010

Related U.S. Application Data

(63) Continuation of application No. 10/993,706, filed on Nov. 19, 2004, now abandoned.

(51) Int. Cl.
*A61B 17/00*    (2006.01)

(52) U.S. Cl.
USPC ........................................... 606/84

(58) Field of Classification Search
USPC ............... 606/79, 82, 84, 85; 30/278, 279.2, 30/280
See application file for complete search history.

(56) References Cited

U.S. PATENT DOCUMENTS

| | | | | |
|---|---|---|---|---|
| 13,901 | A * | 12/1855 | Chapman | 12/104.5 |
| 86,741 | A * | 2/1869 | Dutton | 30/279.6 |
| 117,839 | A * | 8/1871 | Watt | 12/104.5 |
| 1,015,461 | A * | 1/1912 | Vlcheck | 30/169 |
| 1,991,267 | A * | 2/1935 | Waldron et al. | 30/280 |
| 2,876,777 | A | 3/1959 | Kees, Jr. | 606/84 |
| 3,512,519 | A * | 5/1970 | Hall | 600/567 |
| 4,203,444 | A | 5/1980 | Bonnell et al. | 128/276 |
| 4,586,496 | A | 5/1986 | Keller | 128/92 E |
| 4,601,290 | A | 7/1986 | Effron et al. | 128/305 |
| 5,857,995 | A * | 1/1999 | Thomas et al. | 604/22 |
| 6,425,920 | B1 | 7/2002 | Hamada | 623/17.16 |
| 6,610,089 | B1 | 8/2003 | Liu et al. | 623/17.11 |
| 6,679,917 | B2 | 1/2004 | Ek | 623/20.14 |
| 2003/0216669 | A1 | 11/2003 | Lang et al. | 600/587 |
| 2006/0111722 | A1 | 5/2006 | Bouadi | 606/79 |

* cited by examiner

*Primary Examiner* — Anu Ramana

(74) *Attorney, Agent, or Firm* — Sunstein Kann Murphy & Timbers LLP

(57) ABSTRACT

The present invention pertains generally to a surgical tool for cutting and shaping bone, cartilage and other anatomical structures. In particular, described herein are surgical tools having at least two cutting surfaces.

7 Claims, 4 Drawing Sheets

SURGICAL CUTTING TOOL

CROSS-REFERENCE TO RELATED APPLICATIONS

This application is a continuation of U.S. patent application Ser. No. 10/993,706, filed Nov. 19, 2004, entitled "Surgical Cutting Tool," which is hereby incorporated herein by reference in its entirety.

TECHNICAL FIELD

The present invention pertains generally to medical devices, particularly surgical tools for cutting and shaping bone, cartilage and other anatomical structures. In particular, surgical tools having at least two cutting surfaces are provided.

BACKGROUND ART

Generally, joint surgery, such as implantation of prostheses, includes cutting of bone and cartilage tissue. For example, total knee replacement (TKR) involves surgical resection of the entire or the majority of the articular surface of one or more bones. With these procedures, the marrow space is reamed in order to fit the stem of the prosthesis. Less invasive joint arthoplasties, such as those described in U.S. Patent Publication No. 20030216669 also will generally involve some shaping of the cartilage and/or bone in the target joint.

Various tools are currently available for cutting cartilage and bone. Commercially available osteotomes typically have a single straight or curved cutting surface. See, e.g., HOKE, HIBBS, and LAMBOTTE osteomes available from Miltex, Inc. (York, Pa.); tools available from Biomet, Inc (Warsaw, Ind.); U.S. Pat. No. 4,586,496 to Keller; and U.S. Pat. No. 4,601,290 to Effron et al.

Surgical tools having a cylindrical cutting surface have also been described. See, e.g., U.S. Pat. No. 4,203,444 to Bonnell and U.S. Pat. No. 6,679,917. However, cylindrical configuration of the rotating cutting edges typically creates a depression with a curved, concave surface, as opposed to a box-like depression with more or less flattened sides. As much as the surgeon may attempt to match the equator of the concavity, removal of additional tissue always leaves behind a ridge or protrusion on the treated surface. Such protrusions are particularly disadvantageous in joint surgery where jagged or protruding surfaces on cartilage or bone can inhibit free joint movement and lead to pain and inflammation after surgery.

Thus, there remains a need for surgical cutting devices that readily create a cartilage or bone surface that is more or less normal in topography for the joint or region being treated after desired tissue is removed, thereby avoiding the production of ridges, protuberances or odd shaping that may hinder or make joint movement painful after surgery. There is a further need for a surgical cutting device that permits more efficient cutting and sculpting of tissue in order to reduce the duration of surgery.

SUMMARY OF THE INVENTION

It is a general object of the invention to provide a surgical cutting device that is capable of creating a substantially normal surface after tissue removal. More specifically, the invention provides a versatile and efficient surgical cutting tool that removes cartilage and/or bone in two directions. Furthermore, the cutting blades may be curved in either a convex or concave orientation (relative to the surface to be cut), thereby allowing the blades to conform to bone and cartilage curvature or create a desired curvature that better fits an implant.

In one aspect, the invention includes a surgical device for cutting and removing target tissue such as cartilage and bone within a body, the device comprising: a handle; and a cutting element attached to the handle, the cutting element comprising at least two cutting surfaces, wherein the cutting surfaces cut tissue when the device is pushed or pulled along the target tissue. In certain embodiments, the cutting surfaces are blades, abrasion surfaces, or combinations thereof. One or more cutting surfaces can be disposed on opposite sides of the cutting element or, alternatively, one or more cutting surfaces can be disposed on the same side of the cutting surface.

Any of the devices described herein may further comprise a carrier, wherein the cutting element is disposed within the carrier.

In any of the devices described herein, the cutting element may be curved on one or both of the two cutting surfaces.

In another aspect, the invention includes a surgical device for cutting and removing target tissue such as cartilage and bone within a body, the device comprising: a handle; and cutting means attached to the handle, the cutting means comprising at least two cutting surfaces, wherein the cutting means cuts tissue when the device is pushed or pulled along the target tissue. In certain embodiments, the cutting means is curved one or both of the two cutting surfaces.

In another aspect, the invention includes a kit comprising one or more surgical devices described herein and one or more joint implants.

In yet another aspect, the invention includes a surgical device for revising a cartilage surface comprising: a handle; a carrier attached to a proximal end of the hand position substantially within a plane; and a cutting element disposed within the carrier such that a blade of the cutting element is at an angle relative to the plane of the carrier. In certain embodiments, the handle and the cutting element are formed integrally. In other embodiments, the cutting element is removable. In any of the devices described herein, the cutting element may have a plurality of blades, for example at least two.

In any of the devices described herein, the cutting element may comprise two cutting surfaces disposed such that the surfaces oppose each other. In addition, in any of the devices described herein, the cutting surfaces may be pivotally mounted.

These and other objects and advantages of the invention will become more fully apparent when the following detailed description of the invention is read in conjunction with the accompanying drawings.

DETAILED DESCRIPTION OF SPECIFIC EMBODIMENTS

The present disclosure relates to surgical devices capable of cutting and removing body tissue such as cartilage and bone from a joint region or similarly restricted interior space within the body. The surgical instrument includes a cutting element (optionally housed within a carrier) sized for insertion into a joint or similar restricted interior space within the body and having a first and second end. At least two cutting surfaces protrude from the cutting element. The operator shaves the selected tissue by moving the cutting elements against the tissue via movement of a handle attached to the cutting element. The movement of the device by the operator shaves and/or abrades away tissue depending on the direction of movement and the configuration of the cutting surfaces.

Figure 1:
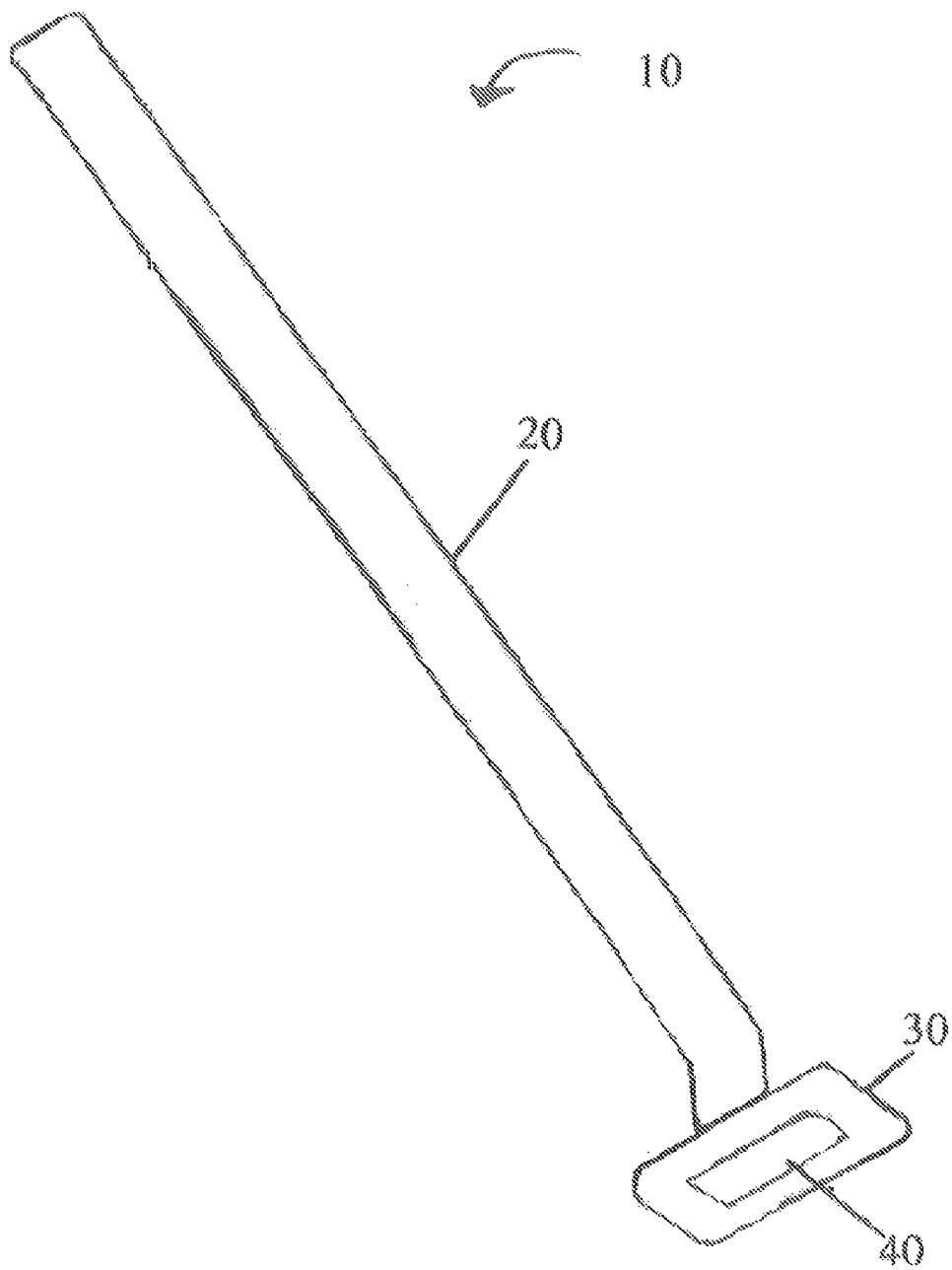
FIG. 1 is a perspective view of an exemplary embodiment of the surgical device of the invention.

Turning now to FIG. 1, the surgical device of the invention will now be described. For the purposes of the following disclosure, the end of the device that is closest to or in contact with the patient is designated the distal end. The end closest to the surgeon is designated the proximal end.

Figure 2:
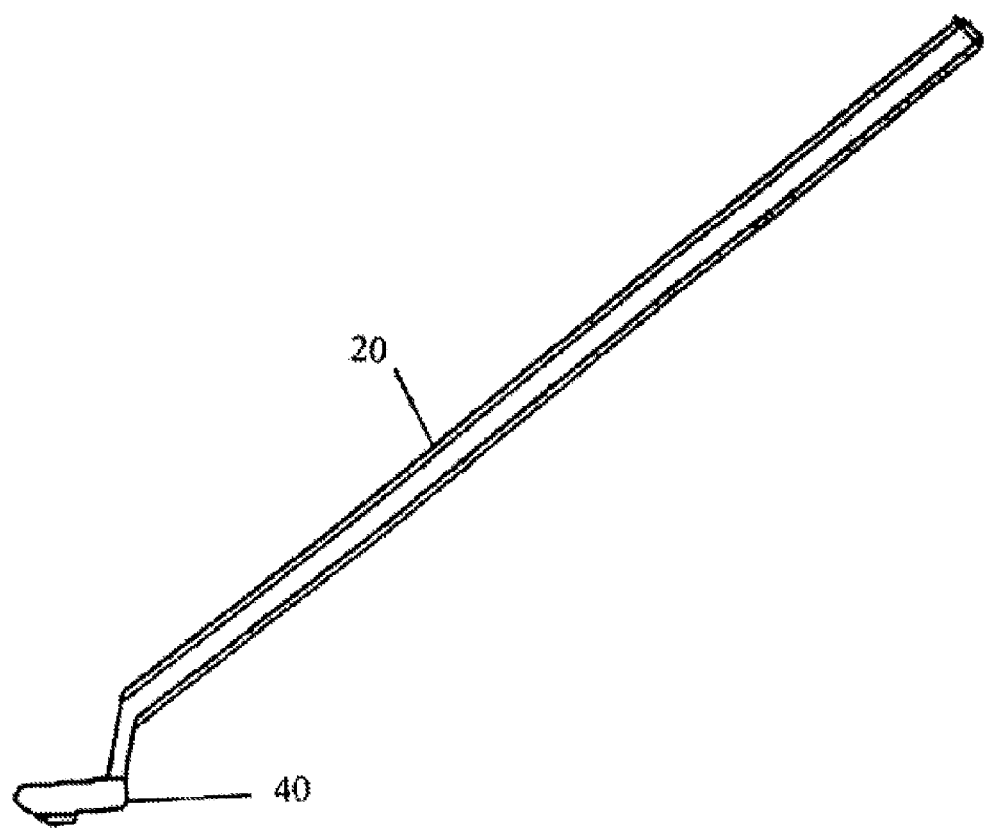
FIG. 2 is a side view of an exemplary embodiment of a surgical cutting tool as described herein.
Figure 4:
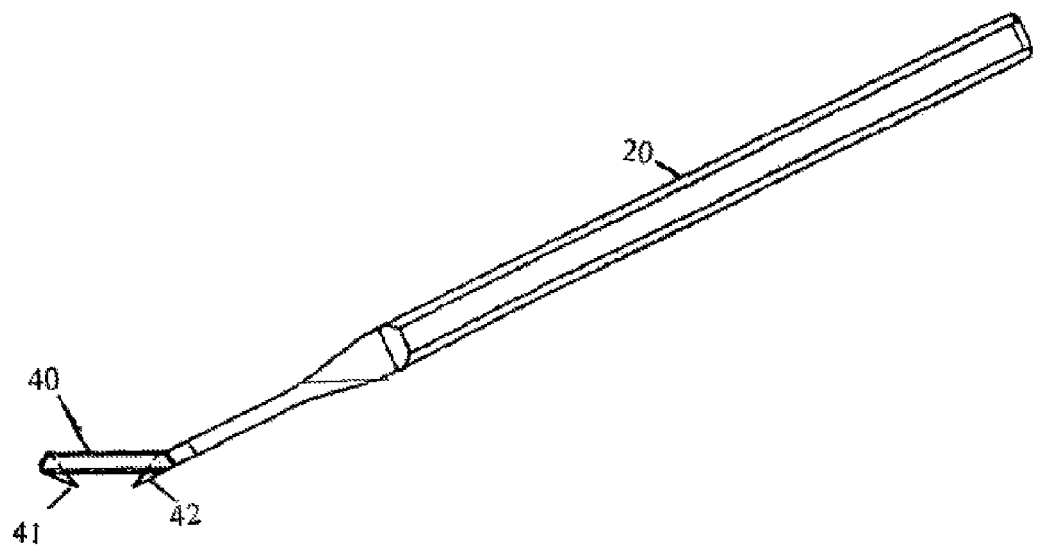
FIG. 4 is a side view of another exemplary device.
Figure 6:
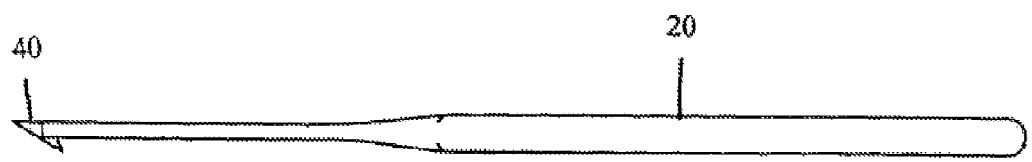
FIG. 6 is a side view of another exemplary device.

The surgical device (10) includes a handle (20), an optional carrier for the cutter (30) and a cutting element 40. During cutting, the operator (surgeon) actuates the device by gripping handle (20) and contacting cutting element (40) with the surface to be shaved. Handle (20) may be straight (FIGS. 4 and 6) or include one or more angled or curved portions (FIGS. 1 and 2). Handle (20) may be made of a wide variety of materials, including but not limited to, metals, polymers, alloys and combinations thereof so long as the material is not harmful to the patient (e.g., toxic, etc.).

Cutting element (40) is attached to the distal end of the handle (20) directly or may be placed in a carrier (30) that is attached to the distal end of the handle (20). In certain embodiments, cutting element (40) is disposed with in a carrier (30) such that the cutting element (40) can be readily replaced. In certain embodiments, cutting element (40) (or carrier (30) containing the cutting element (40)) is fixedly attached to handle (20) and does not move in relation to the handle. Alternatively, cutting element (40) may be moveable in relation to the handle (20) for example by using springs, hinges or other moveable attachment mechanisms.

Figure 3:
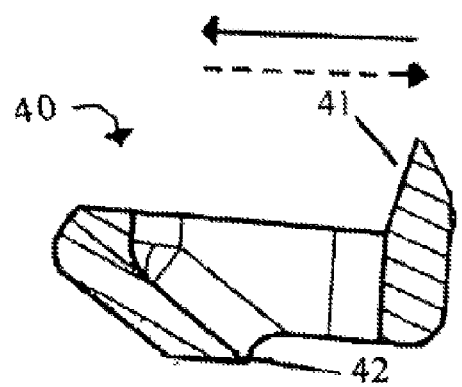
FIG. 3 is detailed side view of an exemplary cutting element.
Figure 5:
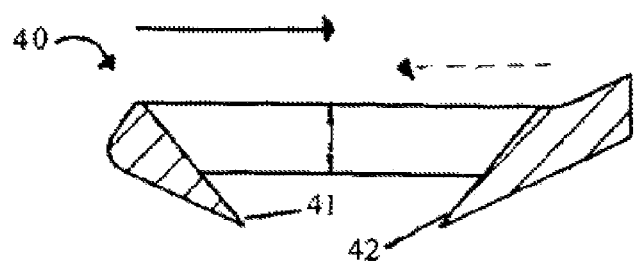
FIG. 5 is a detailed side view of another exemplary cutting element.
Figure 7:
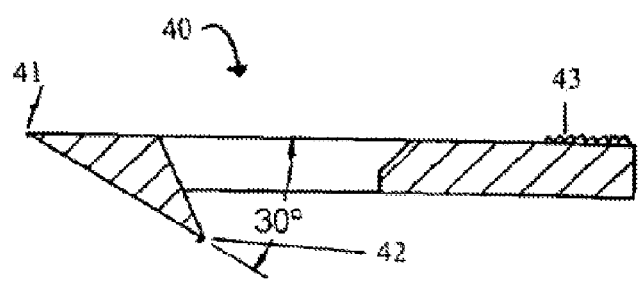
FIG. 7 is a detailed side view of another exemplary cutting element.

Cutting element comprises two or more cutting surfaces (41, 42) that contact the surface (cartilage or bone) to be shaved. Cutting surfaces (41, 42) typically blade-like structures that extend outward from cutting element (40). Cutting surfaces (41, 42) may be variously configured to achieve different cutting styles and surface sculpturing. FIG. 3 shows cutting element (40) in which cutting surfaces (41, 42) are disposed on either end of the cutting element (40) and in which cutting surfaces (41, 42) are on opposite sides of cutting element (40). FIG. 5 shows a variation in which cutting surfaces (41, 42) are disposed on either end of the cutting element (40) and in which cutting surfaces (41, 42) are on the same side of the cutting element (40) and are angled toward each other. FIG. 7 shows cutting element (40) having cutting surfaces (41, 42) disposed at the distal end of cutting element (40). It will be appreciated any combination of angled, opposed, facing and other configurations of two or more cutting surfaces may be used in a single device.

In addition to blade cutting surfaces (41, 42), cutting element may also includes one or more surfaces (43) that can be used to achieve different abrasive effects. For example, serrated surfaces, ridges, teeth-like surfaces or any other projections may be included, all as shown in FIG. 7. Blade-like cutting surfaces (41, 42) and abrasive cutting surfaces (43) can be used in combination together during the cutting procedure much like a carpenter's plane, removing pieces of tissue and then smoothing over the surface to achieve a substantially planar surface after treatment.

Other configurations, such as those with concave and convex surfaces, can also be provided for situations in which the surgeon wishes to leave behind a curved surface after tissue removal is completed.

In variations in which the cutting surfaces (41, 42) are angled (e.g., with respect to the cutting element as a whole), it will be apparent that the angles can vary greatly, for example between about 10° and about 120° (or any value therebetween), more preferably between about 20° and about 90° (or any value therebetween), and even more preferably, between about 20° and about 40° (or any value therebetween). For example, as depicted in FIG. 2, the angle of cutting surface (41) in relation to cutting element (40) is approximately 35°. FIG. 5 depicts a variation in which the angles of the cutting surfaces (41, 42) are 26° and 25°, respectively. FIG. 7 depicts a variation in which cutting surface (42) is angled at approximately 30°, relative to the linear cutting element (40).

Cutting element (40) and, hence, cutting surfaces (41, 42) can be made out of any suitable material that is both strong and resistant to shocks and stresses encountered in surgery. Further, the composition of the material should not contain biotoxic elements or compounds. In this regard, the chrome content of the composition is preferably less than about 10%. Preferably, the composition must also have a Knoop hardness of 466 or greater in order to ensure continued cutting efficiency. A number of compositions meet or exceed these specifications including ceramics such as Alumina, Zirconia, MgO partially stabilized TTZ, and tempered titanium. Injection molded materials may be also be employed.

The overall dimensions of the device will vary depending on the application and target surface. For example, a device to be used in a typically knee arthroplasty will range in length (distal to proximal ends) from approximately 100 mm to 200 mm (and any value therebetween) and more preferably between about 120 mm and 170 mm (or any value therebetween). Similarly, the cutting element in a device used in knee surgery is generally between about 10 mm and 20 mm (or any value therebetween) in length and between about 2 and 20 mm wide (or any value therebetween). It will be apparent that the devices as a whole or elements thereof can be made larger or smaller for other indications. For example, the handle dimensions may remain fairly constant in order for the operator to maintain a grip, while the carrier and/or cutting elements are dimensioned so as to be maneuvered within the space to be operated on.

The tools described herein are used in conjunction with conventional surgical techniques, including arthroscopic and laproscopic procedures. Specifically, the instrument may be inserted into the selected joint through an incision, or can be applied directly to the treatment site if the treatment site is already exposed. As pressure is applied by the surgeon to the cutting element (via the handle), cartilage and/or bone is abraded away.

As noted above, the devices described herein include cutting surfaces that are capable of cutting tissue when the device is both pushed and pulled along a target surface. As depicted in FIG. 3 for example, cutting surface (41) will shave target tissue on one side of the cutting element (40) when the device is moved in the direction of the solid arrow and cut tissue on the other side of the cutting element (40) when cutting surface (42) is moved by the operator in the direction of the dashed arrow. FIG. 5 shows another variation in which tissue on the same side cutting element (40) is cut when the device is moved in either direction. In particular, when the device is moved in the direction of the solid arrow, cutting element (41) shaves the target tissue. When the device is moved in the direction of the dashed arrow, cutting element (42) shaves the target tissue. Thus, in either axial direction, the cutting and/or shaping of the target tissue (e.g., cartilage and/or bone) is achieved.

It will be appreciated that the operation of the cutting device of the present invention differs considerably from that of currently available devices. Because the devices described herein cut when moved in both lateral directions (pushed and pulled), a surgeon can much more easily remove target. In addition, unlike rotating abrading devices, such as burs, which are suited to more planar surfaces and tend to jump or skip over curved surfaces without satisfactory cutting, the configuration of the cutter element and cutting surfaces can be satisfactorily applied to areas of the joint with strong curvature.

The operation of the invention also permits versatility in surface sculpturing. Unlike conventional devices that may leave behind sharp ridges and valleys, the devices described herein can be used to shape surfaces more precisely, whether they be flat or curved. This sculpturing capacity is particularly important in the field of joint repair and reconstruction where the finished joint surface is critical to operation and well being of the repaired joint. Irregular surfaces frequently left behind by conventional devices often result in inflammation, pain, loss of mobility and recurrence of pathology that the operation was originally intended to cure.

The ability of the devices described herein to efficiently cut and shape surfaces such as bone and cartilage with greater precision is particularly useful in the context of minimally invasive joint reconstructions, for example as disclosed in U.S. Patent Publication No. 20030216669. Thus, in certain aspects, the invention includes a kit comprising one or more of the tools described herein in combination with one or more implants. The kits can include other materials, for example, instructions, reagents, containers and/or imaging aids.

Modifications of the procedure and devices described above, and the methods of using them in keeping with this invention will be apparent to those having skill in this mechanical and surgical art. These variations are intended to be within the scope of the claims that follow.

What is claimed is:

1. A method of using a surgical device for cutting and removing target tissue of an articular joint such as cartilage and bone within a body, said method comprising:

cutting tissue of the joint in a first direction with a cutting element having a first cutting surface, cutting tissue of the joint in a second direction with a second cutting surface of the cutting element, wherein the second direction is generally opposite the first direction and the second cutting surface is generally opposed to the first cutting surface such that the cutting surfaces cut tissue when the device is pushed or pulled along the target tissue; and wherein the cutting of the joint tissue with the first and second cutting surfaces results in a smoothing of an articular surface that is substantially devoid of ridges and protuberances.

2. The method of claim 1, wherein said cutting tissue of the joint in a first direction further comprises pushing said cutting element wherein said first cutting surface is a blade.

3. The method of claim 1, wherein said cutting tissue of the joint in a second direction further comprises pulling said cutting element wherein said second cutting surface is a blade.

4. The method of claim 1, wherein said cutting tissue of the joint in a first direction further comprises pushing said first cutting surface in a first direction along the target tissue and said cutting tissue of the joint in the second direction further comprises pulling said second cutting surface in a second direction along the target tissue wherein said first cutting surface and said second cutting surface are blades.

5. The method of claim 1, wherein said cutting tissue of the joint in a first direction further comprises pushing said cutting element wherein said first cutting surface is an abrasion surface.

6. The method of claim 1, wherein said cutting tissue of the joint in a second direction further comprises pulling said cutting element wherein said second cutting surface is an abrasion surface.

7. The method of claim 1, wherein said cutting tissue of the joint in a first direction further comprises pushing said first cutting element having an abrasion surface in a first direction along the target tissue and said cutting tissue of the joint in the second direction further comprises pulling said second cutting surface in a second direction along the target tissue wherein said first cutting surface and said second cutting surface are abrasion surfaces.

* * * * *